United States Patent [19]

Arai et al.

[11] Patent Number: 4,919,890
[45] Date of Patent: Apr. 24, 1990

[54] DRY TYPE ANALYSIS ELEMENT

[75] Inventors: Fuminori Arai, Saitama; Fusae Osada, Kanagawa, both of Japan

[73] Assignee: Fuji Photo Film Co., Ltd., Kanagawa, Japan

[21] Appl. No.: 177,287

[22] Filed: Apr. 4, 1988

[30] Foreign Application Priority Data

Apr. 2, 1987 [JP] Japan .................................. 62-82061
Apr. 3, 1987 [JP] Japan .................................. 62-82285

[51] Int. Cl.$^5$ .............................................. G01N 1/48
[52] U.S. Cl. ........................................ 422/56; 422/57; 436/135; 436/170; 436/810; 435/28; 435/805; 435/810
[58] Field of Search ................ 422/56, 57, 58; 435/7, 435/11, 14, 28, 805; 436/135, 169, 170, 810

[56] References Cited

U.S. PATENT DOCUMENTS

| | | | |
|---|---|---|---|
| 4,089,747 | 5/1978 | Bruschi | 435/25 |
| 4,547,461 | 10/1985 | Esders et al. | 422/56 |
| 4,604,264 | 8/1986 | Rothe et al. | 422/56 |
| 4,665,023 | 5/1987 | Deneke et al. | 436/135 |
| 4,788,140 | 11/1988 | Findley et al. | 422/56 |
| 4,812,399 | 3/1989 | Mauck et al. | 435/28 |

*Primary Examiner*—Barry S. Richman
*Assistant Examiner*—Gregory R. Muir
*Attorney, Agent, or Firm*—Sughrue, Mion, Zinn, Macpeak & Seas

[57] ABSTRACT

A dry type analysis element for detecting a specific constituent in a liquid is provided. The dry type analysis element comprises a light-transmissive support having thereon at least one water-penetrative layer, at least one of said water-penetrative layer(s) containing a composition capable of interacting with said specific constituent in said liquid, wherein said composition contains a leuco dye comprising at least one compound selected from the group consisting of compounds represented formula [I] and salts of these compounds

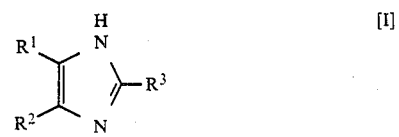

wherein $R^1$ represents a substituted or unsubstituted aryl group, $R^2$ represents a substituted or unsubstituted alkyl group, and $R^3$ represents a substituted or unsubstituted aryl group, and said leuco dye is dissolved in a hydrophobic solvent to form a solution that is contained in said water-penetrative layer as a dispersion in a hydrophilic medium.

17 Claims, No Drawings

DRY TYPE ANALYSIS ELEMENT

FIELD OF THE INVENTION

The present invention relates to a dry type analysis element useful for detecting and quantitatively determining a specific constituent in a liquid. The present invention particularly relates to a dry type analysis element suitable for detecting a specific constituent in a liquid that can produce hydrogen peroxide or can be involved in a reaction that produces hydrogen peroxide.

BACKGROUND OF THE INVENTION

Various analytical methods have been known for quantitatively determining a specific constituent in a liquid by detecting hydrogen peroxide resulting from a reaction involving the specific constituent. Among them are methods of using leuco dyes containing an imidazole nucleus as described in U.S. Pat. No. 4,089,747 and Japanese Patent Application (OPI) No. 193352/1984 ("OPI" means a published unexamined Japanese patent application).

These leuco dyes produce 1 mole of dye from 1 mole of hydrogen peroxide, and since the dye has a high molecular extinction coefficient, the detection sensitivity is advantageously high. However, it is disadvantageous that the discoloring of the dye is relatively high.

SUMMARY OF THE INVENTION

An object of the present invention is to substantially eliminate the discoloring of oxidized products of leuco dyes contained in a dry type analysis element for quantitatively determining a specific constituent in a liquid by using leuco dyes having an imidazole nucleus to detect hydrogen peroxide resulted from a reaction involving the constituent.

It has been found that the above technical problem has been solved by providing a dry type analysis element for detecting a specific constituent in a liquid, which comprises a light-transmissive support having provided thereon at least one water-penetrative layer, at least one of said water-penetrative layer(s) containing a composition capable of interacting with said specific constituent in said liquid, wherein said composition contains a leuco dye comprising at least one compound selected from the group consisting of compounds represented formula [I] and salts of these compounds

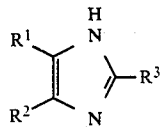
[I]

wherein $R^1$ represents a substituted or unsubstituted aryl group, $R^2$ represents a substituted or unsubstituted alkyl group, and $R^3$ represents a substituted or unsubstituted aryl group,
and said leuco dye is dissolved in a hydrophobic solvent to form a solution that is contained in said water-penetrative layer as a dispersion in a hydrophilic medium.

DETAILED DESCRIPTION OF THE INVENTION

Substituents that may be possessed by the aryl group represented by $R^1$ such as a phenyl group include, for example, a hydroxy group, an alkoxy group, an amino group, an alkylamino group, and a dialkylamino group. The alkyl moiety in these substituents preferably has 1 to 3 carbon atoms. A dialkylamino group such as a dimethylamino group and a diethylamino group is preferred.

The alkyl group represented by $R^2$ preferably has from 1 to 3 carbon atoms and it can be, for example, a methyl group or an ethyl group. It may be unsubstituted or substituted, for example, by a phenyl group, a phenoxy group, or a 4-dimethylaminophenyl group.

Substituents that may be possessed by the aryl group represented by $R^3$ include, for example, a hydroxy group, an alkoxy group (preferably having 1 to 4 carbon atoms), and a halogen atom such as a bromine atom and a chlorine atom.

Typical examples of the aryl group represented by $R^1$ are a 4-dimethylaminophenyl group and a 4-diethylaminophenyl group. Typical examples of the alkyl groups represented by $R^2$ are a benzyl group and a phenetyl group, with a phenetyl group preferable. Typical examples of the aryl group represented by $R^3$ are a 4-hydroxyphenyl group and a 3,5-dimethoxy-4-hydroxyphenyl group.

Methods of synthesizing the above leuco dyes are described in Japanese Patent Application (OPI) No. 193352/1984.

Dry type analysis elements suitable for quantitatively determining biochemicals contained in body fluids have been known and are described, for example, in Japanese Patent Application (OPI) Nos. 53888/1974 (corresponding to U.S. Pat. No. 3,992,158), 164356/1980 and 102388/1984. Generally, in dry type analysis elements, the amount of a reaction product or an unreacted component of a reaction between an analyte constituent and a reagent in the analysis element is measured optically. This is done, for example, by measuring spectrophotometrically the color development, color change, fluorescence, emission or the like to determine quantitatively the analyte constituent. When a dry analysis element is used, a specific constituent in a body fluid such as a biochemically active substance can be analyzed simply, quickly and precisely.

The present analysis element comprises at least one water-penetrative layer, preferably at least two water-penetrative layers, and may not have a support, but preferably has a support. Preferably, the support is light-transmissive and in addition water-impenetrable.

Oxidized products of leuco dyes may be produced by the interaction between a specific constituent in a sample fluid and a composition in an analysis element or they may be produced by the interaction between individual components in an analysis element involving such a specific constituent, which for example acts as a catalyst. The interaction may comprise a single reaction or several reactions. The term "interaction" means chemical or physical interactions of any types that is capable of producing a detectable dye whose chemical activity, catalytic activity (as in the formation of an enzyme/substrate composite), immunogenic activity (as in the antigen/antibody reaction), or concentration shows directly or indirectly the concentration or the presence of a specific analyte substance.

The interaction composition is selected on the basis of a specific analysis system. For example, the activity of an enzyme in a sample liquid is to be determined, it is required that the interaction composition contains a substrate for the enzyme. If the analyte constituent in a sample liquid is a substrate for an enzyme, analysis can be carried out by having the interaction composition containing an enzymatically active substance for the substrate.

The interaction composition useful in the present invention contains a substance having for example, oxidase activity. Enzymes such as oxidase active substances for example glucose oxidase, glycerol oxidase, and cholesterol oxidase can be contained in a reagent layer or a liquid spreading layer (which will be described later) of the analysis element. The element can then be used for the analysis of constituents that are the substrates for such enzymes. These substrates can also be applied to the analysis of enzymes, substrates, antigens, antibodies, etc. resulting from other enzyme reactions or immunoreactions (antigen-antibody reactions).

As the hydrophobic solvents, hydrophilic mediums, and dispersing methods use can be made of known hydrophobic solvents, hydrophilic mediums and dispersing methods as described hereinafter.

Specific examples of leuco dyes useful in the invention are given below:

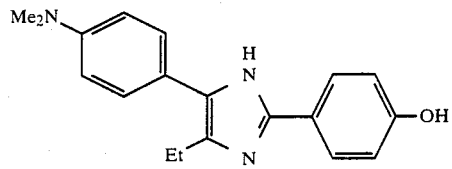
(1)

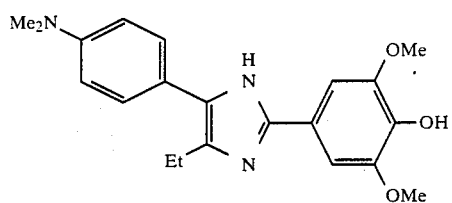
(2)

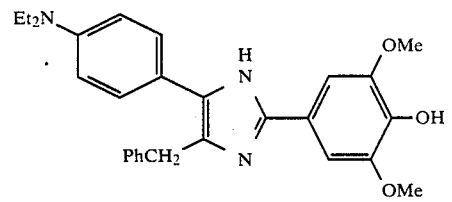
(3)

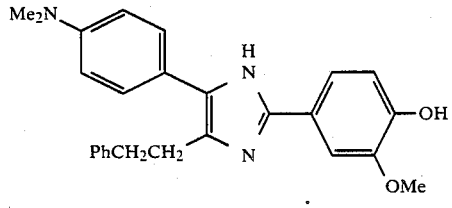
(4)

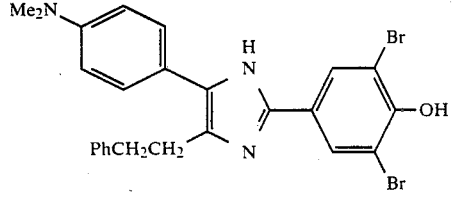
(5)

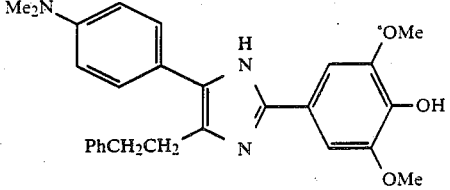
(6)

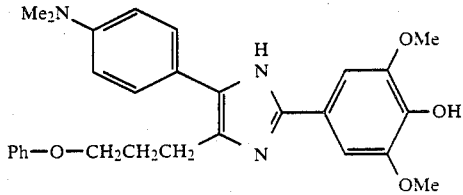
(7)

The compounds represented by formula (I) and acid salts thereof each may be used solely or may be used in a mixture thereof. The leuco dye of the present invention may consist of at least two acid salts of at least one compound selected from the compounds represented by the formula (I). At least two acid salts mentioned above preferably have different acid components. When the salts are used in such a combination the color development of the analysis element is further improved in prevention from the change during the storage of the element, even when it is stored at a freezing temperature. Further, mixed salts are more readily dissolved than a single salt in a hydrophilic solvent. The acids maybe inorganic acids or organic acids, or combinations thereof. For example, the acids may be selected from hydrochloric acid, nitric acid, acetic acid, oxalic acid, citric acid, benzoic acid, salicylic acid, phthalic acid, etc. Although the mixing ratio of the acids is not particularly limited, it is preferably that each acid is used in an amount of 5 mol % or more, and more preferably one of the acids is used in a ratio of from 10 to 25 mol % based on the total amount of acids.

The above described leuco dye is contained in at least one water-penetrative layer of a dry-type analysis element. Although the water-penetrative layer may be a porous layer, it is preferable that the water-penetrative layer is a non-porous layer using a hydrophilic polymeric binder. As the hydrophilic polymer, use can be made, for example, of gelatin, and its derivatives (e.g., phthalated gelatin), cellulose derivatives (e.g., hydroxymethyl cellulose), agarose, acrylamide polymers, methacrylamide polymers, and copolymers of vinyl monomers with acrylamide or methacrylamide.

The leuco dye is contained in the continuous phase of the hydrophilic polymer as a dispersion of a solution wherein the dye is dissolved in a hydrophobic solvent. As the hydrophobic solvents use can be made of hydrophobic solvents generally used in multi-layered gelatin/silver halide color photographic materials. For example, solvents described in U.S. Pat. No. 2,322,027 can be used. Examples of such solvents include phthalic acid diesters such as dibutyl phthalate, dicyclohexyl phthalate, di-2-ethylhexyl phthalate, and decyl phthalate; phosphates such as triphenyl phosphate, tricresyl phosphate, 2-ethylhexyldiphenyl phosphate, tricyclohexyl phosphate, and tri-2-ethylhexyl phosphate; benzoates such as 2-ethylhexylbenzoate; amides such as N,N-diethyllauryamide and N-tetradecylpyrrolidone; phenols such as 2,4-di-t-amylphenol, fatty acid esters such as trioctyl citrate; hydrocarbons such as paraffins; and halogenated hydrocarbons such as chlorinated paraffins, which are generally high boiling point solvents.

The leuco dye can be dissolved in a high boiling point solvents or in a mixture of a high boiling point solvent and a low boiling point solvent. Alternatively, the leuco dye may be first dissolved in a low boiling point solvent and then may be mixed with a high boiling point solvent. As the low boiling point solvents, use can be made of organic solvents having a boiling point of from 50° C. to 160° C. Examples thereof include fatty acid esters such as ethyl acetate, butyl acetate, and 2-ethoxyethyl acetate; ketones such as methyl ethyl ketone; and amides such as dimethylformamide.

To disperse the solution of a leuco dye in an aqueous solution of the hydrophilic polymer, various known dispersing methods, particularly those dispersing methods suitable for preparing oil-in-water type dispersions, can be used. To effect the dispersion of the dyes, it is preferable to use a surface active agent such as sodium dodecylbenzene sulfonate.

The concentration of the leuco dye in the hydrophobic solvent solution is preferably from about 0.5 to 10%. The concentration of the hydrophilic polymer in the polymer solution is preferably from about 0.5 to 20%, and the amount of the leuco dye in the dispersion is preferably from about 0.05 to 3%. The amount of the leuco dye in the water-penetrative layer is generally from about 0.5 to 10% by weight based on the weight of the material which consitutes the layer in a dry state.

The present invention can be applied to various known dry type analysis elements. The element may have a multi-layered constitution on a support including a porous layer, a reagent layer, a spreading layer, a detecting layer, a light screening layer, a binding layer, a filtering layer, a water absorbing layer, an undercoat layer, and other layers. As such analysis elements can be mentioned those described in U.S. Pat. Nos. 3,992,158 and 4,042,335 and Japanese Patent Application (OPI) No. 164356/1980.

When a light-transmissive and water-impenetrable support is used, practicable constitutions of the present dry type analysis element are:

(1) those having provided on a support a reagent layer and a spreading layer thereon, (2) those having provided on a support a detecting layer, a reagent layer and a spreading layer in the stated order, (3) those having provided on a support a reagent layer, a light reflecting layer, and a spreading layer in the stated order, (4) those having provided on a support a detecting layer, a reagent layer, a light reflecting layer, and a spreading layer in the stated order, (5) those having provided on a support a detecting layer, a light reflecting layer, a reagent layer, and a spreading layer in the stated order, (6) those having provided on a support a second reagent layer, a light reflecting layer, a first reagent layer, and a spreading layer in the stated order, and (7) those having provided on a support a detecting layer, a second reagent layer, a light reflecting layer, a first reagent layer, and a spreading layer in the stated order.

When a detecting layer is provided in the element the colored dye formed from the leuco dye diffuses to the detecting layer, and it is detected through the light-transmissive support. The detecting layer may be comprised a hydrophogic polymer, and it may contain a mordant, for example, a cationic polymer for detecting an anionic dye.

In elements (1) to (5), the reagent layer may consist of plural different layers. The leuco dye may be incorporated to one or more of reagent layers. A water absorbing layer may be provided between the support and the reagent layer or the detecting layer. In elements (1) to (3) and (6), a filtering layer may be provided between the reagent layer and the detecting layer or the spreading layer. In elements (3) to (7), a filtering layer may be further provided between the light reflecting layer and the detecting layer, between the reagent layer or the spreading layer, between the reagent layer and the detecting layer, or between the reagent layer and the spreading layer. If the reagent layer consists of plural layers, a filtering layer may further be provided between each of the reagent layers.

The present invention is useful for quantitatively determining various analyte substances in whole blood, plasma or blood serum. For example, the present invention is useful for quantitatively determining metabolites such as glucose, cholesterol, uric acid, glycerol, triglycerides, uric acid, and bilirubin as well as for determining the enzyme activity, for example, of creatine kinases, transaminases (e.g., alanine aminotransferase and asparagine aminotransferase), and hydrolases (e.g., amylase, acid phosphatase, and alkaline phosphatase). The present invention can also be used for immunological analysis that uses specific antibodies or antigens.

Example of the reagent layer of the present dry type analysis element include a substantially uniform layer using a hydrophilic polymer as a binder, and porous layers (such as fibrous or non-fibrous porous layer) as described, for example, in Japanese Patent Application (OPI) Nos. 70163/1983 (corresponding to U.S. Pat. No. 4,486,537), 4959/1986, 116258/1987, 138756/1987, 138757/1987 and 138758/1987.

The reagent layer may contain all or part of the interaction composition provided that the leuco dye is contained in the reagent layer. In addition to the leuco dye, the reagent layer may contain an enzyme, a coenzyme, a substrate for an enzyme, an oxidant, a buffer, etc.

Examples of buffers that may be contained in the reagent layer include carbonates, borates, phosphates, and buffers described by N. E. Good in *Biochemistry*, Vol.V, No.2, pages 467 to 477 (1966).

These buffers can be selected by referring to publications such as *Biochemistry*, Vol. 5 mentioned above and *Tanpakushitsu Koso no Kisojikken*, (by Takeichi Horio et al, Nankodo, 1981).

When a porous layer is used as a spreading layer, the layer preferably has a liquid metering effect. By "liquid metering effect" it is meant that a liquid sample supplied drop-wise onto the surface of the layer can be spread to the direction of the surface of the layer approximately uniformly per unit area without substantially localizing the constituents contained in the liquid.

Examples of materials constituting the developing layer as well as other porous layers include filter paper, nonwoven fabric, woven fabric (e.g., plane weave fabric), knitted web (e.g., tricot fabric), and glass fiber filter paper. Woven and knitted materials are preferred for the spreading layer. Woven materials may be subjected to glow discharge treatment as described in Japanese Patent Application (OPI) No. 66359/1982. The spreading layer may contain surface active agents or hydrophilic polymers as described in Japanese Patent Application (OPI) No. 222770/1985, Japanese Patent Application Nos. 122875/1986, 122876/1986, and 143754/1986 (the latter three applications correspond to German Patent Application (OLS) No. 3,717,913) in order to control the spreading area, the spreading speed, etc.

A bonding layer for bonding and layering porous layers may be provided on a layer such as a reagent layer, a light reflecting layer, filtering layer, a water absorbing layer and a detecting layer. The bonding layer comprises a hydrophilic polymer capable of bonding the porous layers when swelled with water. Examples of the hydrophilic polymer include gelatin, gelatin derivatives, polyacrylamides, and starches.

The present analysis element may comprise a light reflecting layer. For example, a light reflecting layer may be provided between a reagent layer and a detecting layer or between a reagent layer and a liquid spreading layer. When a detectable change (e.g., a color change or color development) occurs, for example, in the detecting layer or in the reagent layer it is measured by reflecting light from the support side having a light transmissive property. The light reflecting layer functions as a background layer or it serves to reduce the intensity of the color of an analyte liquid supplied as a drop on the spreading layer such as a yellow color of bilirubin or a red color of hemoglobin when the sample is whole blood. It is preferable that the light reflecting layer is a water-penetrative layer which contains a hydrophilic polymeric binder in which light-reflecting fine particles such as titanium oxide, barium sulfate or the like are dispersed. Preferred examples of the binder include gelatin, gelatin derivatives, and polyacrylamides. Curable polymers such as gelatin may contain a hardening agent. The spreading layer, the reagent layer, the detecting layer, and other layers comprising the analysis element may contain, if desired, particles of titanium oxide or the like.

The present analysis element may comprise, in addition to a liquid developing layer, a layer for filtering and removing substantially all blood cells. It is preferable to use for example porous layers as described in Japanese Patent Application (OPI) Nos. 70163/1983 (corresponding to U.S. Pat. No. 4,486,539), 4959/1986, 116258/1987, 198356/1987, 178357/1987, and 178358/1987.

After the application of a sample of whole blood to the element, it is possible to incubate (heat) the element in order to get the test result quickly or precisely.

If in a sample liquid there is a constituent to be analyzed, the constituent and the interaction composition interact at a rate based on the concentration of the constituent in the sample. By passing the analysis element through a suitable apparatus for detecting dyes, either the rate of the formation of the dye or the amount of the dye formed corresponding to the concentration of said constituent is measured. The dyes can be detected by suitable spectrophotometric measuring apparatuses known to those skilled in the art such as those described in U.S. Pat. No. 4,584,275 and Japanese Patent Application (OPI) No. 25583/1986.

The present invention will now be further described with reference to the following Examples. Unless indicated otherwise, all parts, percent, ratios and the like are by weight.

EXAMPLE 1

1-1. Preparation of a Leuco Dye Dispersion

Leuco Dye Solution

A leuco dye solution having the following composition A was prepared.

| A: | 2-(4-hydroxy-3,5-dimethoxyphenyl)-4-[4-(dimethylamino)phenyl]-5-phenetylimidazole (leuco dye) acetate | 4.4 g |
|---|---|---|
| | 2-(4-hydroxy-3,5-dimethoxyphenyl)-4-[4-(dimethylamino)phenyl]-5-phenetylimidazole hydrochloride | 0.6 g |
| | N,N-diethyllaurylamide | 90 ml |

Gelatin Solution

A gelatin solution having the following composition B was prepared.

| B: | Alkali-processed gelatin | 230 g |
|---|---|---|
| | Water | 1400 g |
| | Sodium di-2-ethylhexylsulfosuccinate | 5 g |
| | Bis[(vinylsulfonylmethylcarbonyl) amino]methane | 2.3 g |

Reparation of an Emulsion

Composition A was added to Composition B while Composition B was stirred at about 6000 rpm. by using a TK Autohomomixer (an emulsifier manufactured by Tokushu Kikai Kogyo Corporation), and the stirring was continued for about 30 minutes to prepare an emulsion.

1-2. Coating of a Color Developing Reagent Layer

The above emulsion was applied to a transparent polyethylene terephthalate (PET) film (support) having a thickness of 180 μm and which was undercoated with gelatin, in an amount of 150 g per 1 m², and was dried.

1-3. Spreading Layer

Water was applied onto the surface of the color developing reagent layer approximately uniformly in a ratio of 30 g/m² to make the surface wet. A tricot knitted fabric that had a thickness of about 250 μm and wherein 50-denier PET spun yarn was knitted with 36 gauges was lightly pressed to the wet reagent layer to be laminated to form a porous spreading layer.

1-4. Analysis Slide

The thus obtained multi-layered analysis film was cut into square chips measuring 15 mm on a side. The chip was then placed in a polystyrene slide frame having openings (diameter: 10 mm) at he upper side and lower side as described in Japanese Patent Application (OPI) No. 63452/1982 to prepare an analysis slide.

COMPARATIVE EXAMPLE 1

Example 1 was repeated, except that Composition A was changed to as shown below to prepare an analysis slide wherein the leuco dye was dispersed directly in the gelatin.

| A': | 2-(4-hydroxy-3,5-dimethoxyphenyl)-4-[4-(dimethylamino)phenyl]-5-phenetylimidazole acetate | 4.4 g |
|---|---|---|
| | 2-(4-hydroxy-3,5-dimethoxyphenyl)- | 0.6 g |

| | |
|---|---|
| 4-[4-(dimethylamino)phenyl]-5-phenetylimidazole hydrochloride | |
| methanol | 90 ml |

MEASUREMENT EXAMPLE 1

The discoloration rate was assessed as follows.

10 μl of a potassium ferricyanide solution of 300 mg/dl was applied drop-wise to each of the analysis slides prepared in Example 1 and Comparative Example 1. While the slides were incubated at 37° C., visible light having a central wavelength of 540 μm was reflected from the PET support side and measured to obtain the change in the density of the color development.

The results are given in Table 1.

TABLE 1

| Incuabation Time | Example 1 | Comparative Example 1 |
|---|---|---|
| 0 | 0.25 | 0.25 |
| 30 sec | 0.54 | 0.65 |
| 1 min | 0.69 | 0.82 |
| 2 min | 0.85 | 0.89 |
| 3 min | 0.90 | 0.86 |
| 4 min | 0.90 | 0.80 |
| 5 min | 0.88 | 0.74 |
| 6 min | 0.87 | 0.64 |

As apparent from Table 1, the color development of the analysis element according to the invention by an oxidizing agent is fast and the dye produced discolors less.

Note that the discoloration of the dye formed in Comparative Example 1 is large. When 2-(4-hydroxy-3,5-dimethoxyphenyl)-4,5-bis(p-dimethylaminophenyl)imidazole was used as a leuco dye (Comparative Examples 1.2 and 1.3), if it was formed into a dispersion of a hydrophilic solution similar to the present invention or dispersed directly from a methanol solution, the rate of the discoloration was not changed.

EXAMPLE 2

2-1. Preparation of a Leuco Dye Dispersion

Example 1 was repeated, except that the following:

| | |
|---|---|
| glucose oxidase | 40000 U |
| peroxidase | 70000 U |

(U represents an international unit)

were added to Composition B.

2-2. Color Developing Reagent Layer

The above leuco dye dispersion was applied to a PET support in the same manner as Example 1.

2-3. Light Reflecting Layer

A light reflecting layer composition was applied to the color developing reagent layer to form a layer having a dry thickness of 7 μm. The composition is shown below.

| | |
|---|---|
| alkali-processed gelatin | 2.9 g/m$^2$ |
| rutile titanium dioxide fine particles | 13 g/m$^2$ |
| nonylphenoxypolyglycide (containing | 400 mg/m$^2$ |
| 10 glycidol units on the average) | |

2-4. Spreading Layer

A bonding layer composition was applied to the light reflecting layer and then dried to form a layer having a dry thickness of 5 μm. The bonding layer composition (dispersion) was as follows.

| | |
|---|---|
| alkali-processed gelatin | 6.7 g/m$^2$ |
| nonylphenoxypolyglycide (containing 10 glycidol units on the average) | 600 mg/m$^2$ |

Water was applied to the surface of the above bonding layer in an amount of 30 g/m$^2$ approximately uniformly to make the surface wet. A tricot knitted fabric that had a thickness of about 250 μm wherein 50-denier PET spun yarn was knitted with 36 gauges was lightly pressed onto wet bonding laeyr surface to be laminated to form a porous spreading layer.

A polymer-containing ethanol dispersion was applied on the spreading layer so that the applied amounts were shown below, followed by drying to form a multi-layered analysis film for the quantitative analysis of uric acid:

| | |
|---|---|
| hydroxypropyl cellculose (containing 28 to 30% of methoxy group, and 7 to 12% of hydroxypropoxy group. 2% aqueous solution thereof having a viscosity of 50 cps at 20° C.) | 5 g/m$^2$ |
| nonylphenoxypolyethoxyethanol (having an average of 40 oxyethylene units) | 500 mg/m$^2$ |

2-5. Analysis Slide

The thus obtained analysis film for quantitatively analyzing glucose was cut into square chips measuring 15 mm on a side. The chip was then placed held in a slide frame described hereinabove to prepare a biochemical analysis slide for the quantitative analysis of glucose.

COMPARATIVE EXAMPLE 2

Example 2 was repeated, except that the composition of liquid A was changed as given below, thereby completing an analysis slide wherein the leuco dye was directly dispersed in the gelatin,

| | | |
|---|---|---|
| A': | 4-[4-(dimethylamino)phenyl]-5-phenetylimidazole acetate | 4.4 g |
| | 4-[4-(dimethylamino)phenyl]-5-phenetylimidazole hydrochloride | 0.6 g |
| | methanol | 90 ml |

MEASUREMENT EXAMPLE 2

Plasma sample of a normal person and plasma samples of the normal person to which glucose had been added in amounts of 55 mg/dl, 100 mg/dl, and 212 mg/dl respectively were prepared. The amount of glucose in each of the Samples was accurately determined by the glucose electrode method. 10 μl of each of the plasma Samples were applied drop-wise to the developing layer of each of the biochemical analysis slides prepared above. The slides were incubated for 6 minutes at 37° C., and visible light having a central wavelength of 540 μm was used to determine the optical density of the color development of each analysis slide by measuring the reflected light from the PET support side. The results are given in Table 2.

TABLE 2

| Glucose (mg/dl) | 120 | 175 | 220 | 332 |
|---|---|---|---|---|
| Example 2 | 0.85 | 1.08 | 1.38 | 1.64 |
| Comparative Example 2 | 0.63 | 0.72 | 0.86 | 0.71 |

Discoloration was not observed in Example 2 according to the invention, while discoloration was observed in Comparative Example 2.

EXAMPLE 3

3-1. Preparation of a Leuco Dye Solution

A leuco dye solution having the following composition A was prepared.

| A: | 2-(4-hydroxy-3,5-dimethoxyphenyl)-4-[4-(dimethylamino)phenyl]-5-phenetylimidazole acetate | 4.4 g |
|---|---|---|
| | 2-(4-hydroxy-3,5-dimethoxyphenyl)-4-[4-(dimethylamino)phenyl]-5-phenetylimidazole hydrochloride | 0.6 g |
| | methylene chloride | 10 ml |
| | N,N-diethyllaurylamide | 90 ml |

Gelatin Solution

A gelatin solution having the following composition B was prepared.

| B: | Alkali-processed gelatin | 230 g |
|---|---|---|
| | Water | 1400 g |
| | Glucose oxidase | 40000 U |
| | Peroxidase | 70000 U |
| | Sodium di-2-ethylhexylsulfosuccinate | 5 g |
| | Bis[(vinylsulfonylmethyl-carbonyl)amino]methane | 2.3 g |

Preparation of an Emulsion

An emulsion was prepared in the same manner as in Example 1.

3-2. Coating of a Color Developing Reagent Layer

Coating was conducted in the same manner as in Example 1, 1-2.

3-3. Light Reflecting Layer

A light reflecting layer was provided in the same manner as in Example 2, 2-3.

3-4. Spreading Layer

A spreading layer was provided in the same manner as in Example 2, 2-4.

3-5. Analysis Slide

An analysis slide was prepared in the same manner as in Example 2, 2-5.

EXAMPLE 4

An analysis slide containing a salt of an acid of a leuco dye was prepared in the same way as Example 3, except that the composition of Composition A was changed as shown below:

| A': | 2-(4-hydroxy-3,5-dimethoxyphenyl)-4-[4-(dimethylamino)phenyl]-5-phenetylimidazole acetate | 5.0 g |
|---|---|---|
| | methylene chloride | 10 ml |
| | N,N-diethyllaurylamide | 90 ml |

MEASUREMENT EXAMPLE 3

The storage stability of the analysis elements was assessed as follows.

One group of analysis slides prepared in Example 3 and Example 4 were stored at −20° C. for 1 month and another group of analysis slides prepared in Example 3 and Example 4 were stored at 4° C. for 1 month. The stored slides were compared with respect to the color development.

Plasma samples of a normal person and plasma samples of the normal person to which glucose had been added in amounts of 55 mg/dl, 100 mg/dl, and 212 mg/dl respectively were prepared, and the amount of glucose in each of the samples was accurately determined by the glucose electrode method. 10 of each of the plasma samples were applied drop-wise to the developing layer of each of the biochemical analysis slides that had been stored under the different conditions. The slides were incubated for 6 minutes at 37° C. and visible light having a central wavelength of 540 nm was used to determine the optical density of the color development of each analysis slide by measuring the reflected light from the PET support side. The results are given in Table 3.

TABLE 3

| | | Example 3 | | |
|---|---|---|---|---|
| Analysis Element Number | Concentration of glucose (mg/dl) | Conditions of Storage | | Difference |
| | | 4° C. | −20° C. | |
| 1 | 120 | 0.88 | 0.88 | 0.00 |
| 2 | 175 | 1.13 | 1.10 | 0.03 |
| 3 | 220 | 1.46 | 1.46 | 0.00 |
| 4 | 332 | 1.69 | 1.68 | 0.01 |
| 1 | 120 | 0.85 | 0.85 | 0.00 |
| 2 | 175 | 1.10 | 1.09 | 0.01 |
| 3 | 220 | 1.31 | 1.28 | 0.03 |
| 4 | 332 | 1.64 | 1.43 | 0.21 |

It is apparent from Table 3, that when slides containing a single salt were stored at a low temperature, the color development performance decreased slightly in a high concentration region. On the other hand, when the analysis slides containing mixed salts were stored at a low temperature, no change of the developed color of the leuco dye was observed.

EXAMPLE 5

Example 3 was repeated to prepare glucose analysis slides, except that the salts of the leuco dyes in Composition A in Example 3 were changed as shown in Table 4.

After the analysis slides had been stored for 1 month at −20° C., the color development was measured using plasma containing glucose in an amount of 332 mg/dl.

TABLE 4

| Slide No. | Acetate | Hydrochloride | Benzoate | Difference |
|---|---|---|---|---|
| 1 | 5 g | — | — | 0.22 |
| 2 | 4 g | 1 g | — | 0.02 |
| 3 | 3 g | 2 g | — | 0.01 |
| 4 | 2 g | 3 g | — | 0.01 |
| 5 | — | 5 g | — | 0.36 |
| 6 | — | — | 5 g | 0.41 |
| 7 | — | 1 g | 4 g | 0.04 |

In Table 4, by the term "difference" means the difference between the densities of the color development before and after the storage of the analysis slide. From Table 4, it is apparent that the decrease in the developed color of the analysis slide containing a mixed salt of leuco dye was remarkably less than that of the analysis slide containing a single salt.

EXAMPLE 6

Example 3 was repeated to prepare analysis slides, except that instead of using 10 ml of methylene chloride and 90 ml of N,N-diethyllaurylamide as solvents 100 ml of tricresyl diphosphate was used and the salt of the leuco dye was changed as shown in Tables 5 and 6.

After the analysis slides had been stored for 1 month at $-20°$ C., the color development was measured by using plasma containing glucose in an amount of 332 mg/dl.

TABLE 5

| Slide No. | Acetate | Hydrochloride | Benzoate | Difference |
|---|---|---|---|---|
| 1 | 5 g | — | — | 0.29 |
| 2 | 2.5 g | 2.5 g | — | 0.04 |
| 3 | — | 5 g | — | 0.27 |
| 4 | — | 2.5 g | 2.5 | 0.02 |

TABLE 6

| Slide No. | Acetate | Hydrochloride | Benzoate | Difference |
|---|---|---|---|---|
| 5 | — | 5 g | — | 0.27 |
| 6 | 2.5 | — | 2.5 g | 0.07 |
| 7 | — | — | 5 g | 0.31 |

In Tables 5 and 6, the term "difference" means the difference between the densities of the developed color before and after the storage of the analysis slide. From Tables 5 and 6, it is apparent that the decrease in the developed color of the analysis slide containing a mixed salt of leuco dye was remarkably less than that of the analysis slide containing a single salt.

EXAMPLE 7

When the leuco dye salt (5 g total) shown in Table 5 was dissolved in 100 ml of N,N-diethyllaurylamide, each of the hydrochloride, the acetate and the benzoate was not dissolved at all even at 65° C. From these results it can be recognized that when a mixture of salts is used solubility of the leuco dye can be improved.

While the invention has been described in detail and with reference to specific embodiments thereof, it will be apparent to one skilled in the art that various changes and modifications can be made therein without departing from the spirit and scope thereof.

What is claimed is:

1. A dry type analysis element for detecting a specific constituent in a liquid which comprises a light-transmissive support having thereon at least one water-penetrative layer and at least one of said water-penetrative layer(s) containing a composition capable of interacting with said specific constituent in said liquid, wherein said composition contains salts of a leuco dye comprising at least one compound selected from the group consisting of compounds represented by formula (I)

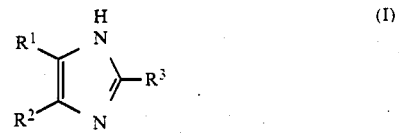

wherein
$R^1$ represents a substituted or unsubstituted aryl group,
$R^2$ represents a substituted or unsubstituted alkyl group, and
$R^3$ represents a substituted or unsubstituted aryl group, said salts being salts of at least two acids and said salts of said leuco dye being dissolved in a hydrophobic solvent to form a solution that is contained in said water-penetrative layer as a dispersion in a hydrophilic medium.

2. A dry type analysis element as in claim 1, wherein the aryl group represented by $R^1$ is a substituted aryl group and the substituent of the aryl group is selected from the group consisting of a hydroxy group, an alkoxy group, an amino group, an alkylamino group, and a dialkylamino group.

3. A dry type analysis element as in claim 1, wherein the aryl group represented by $R^1$ is a phenyl group.

4. A dry type analysis element as in claim 2, wherein said substituent of the aryl group represented by $R^1$ is selected from the group consisting of an alkoxy group, an alkylamino group, and a dialkylamino group and the alkyl moiety in said substituent has from 1 to 3 carbon atoms.

5. A dry type analysis element as in claim 1, wherein the alkyl group represented by $R^2$ has from 1 to 3 carbon atoms.

6. A dry type analysis element as in claim 1, wherein the alkyl group represented by $R^2$ is a substituted alkyl group and the substituent of the alkoxy group is selected from the group consisting of a phenyl group, a phenoxy group and a 4-dimethylaminophenyl group.

7. A dry type analysis element as in claim 1, wherein the aryl group represented by $R^3$ is a substituted aryl group and the substituent of the aryl group is selected from the group consisting of a hydroxy group, an alkoxy group and a halogen atom.

8. A dry type analysis element as in claim 1, wherein the aryl group represented by $R^3$ is a substituted aryl group and the substituent of the aryl group is an alkoxy group having from 1 to 3 carbon atoms.

9. A dry type analysis element as in claim 1, wherein said at least two acids are selected from the group consisting of organic salts and inorganic salts.

10. A dry type analysis element as in claim 1, wherein said at least two acids are selected from the group consisting of hydrochloric acid, nitric acid, acetic acid, oxalic acid, citric acid, benzoic acid, salicylic acid and phthalic acid.

11. A dry type analysis element as in claim 1, wherein each of said at least two acids is used in an amount of at least 5 mol % based on the total amount of acids in said mixture of acid salts.

12. A dry type analysis element as in claim 1, wherein one of said at least two acids is used in a ratio of from 10 to 20 mol % based on the total amount of the acids.

13. A dry type analysis element as in claim 1, wherein the water penetrative layer comprises a hydrophilic polymeric binder.

14. A dry type analysis element as in claim 13, wherein the hydrophilic polymeric binder is a binder selected from the group consisting of gelatin, gelatin derivatives, cellulose derivatives, agarose, acrylamide polymers, methacrylamide polymers, copolymers of vinyl monomers with acrylamide or methacrylamide.

15. A dry type analysis element as in claim 1, wherein the concentration of the salts of the leuco dye in the hydrophobic solvent solution is from 0.5 to 10%.

16. A dry type analysis element as in claim 1, wherein the amount of the leuco dye in the water-penetrative layer is from 0.5 to 10% by weight based on the material which constitutes the layer in a dry state.

17. A dry type analysis element as in claim 1, wherein the element has at least two water-penetrative layers and said leuco dye is contained in at least one of said water-penetrative layer.

* * * * *